United States Patent [19]
Talonn et al.

[11] Patent Number: 5,147,326
[45] Date of Patent: * Sep. 15, 1992

[54] COMBINED SYRINGE AND NEEDLE SHIELD AND METHOD OF MANUFACTURE

[75] Inventors: Daniel A. Talonn, University City; Alan B. Ranford, St. Louis, both of Mo.

[73] Assignee: Sherwood Medical Company, St. Louis, Mo.

[*] Notice: The portion of the term of this patent subsequent to Feb. 18, 2009 has been disclaimed.

[21] Appl. No.: 627,062

[22] Filed: Mar. 1, 1991

Related U.S. Application Data

[63] Continuation-in-part of Ser. No. 212,524, Jun. 28, 1988, Pat. No. 5,053,018.

[51] Int. Cl.$^5$ ............................................. A61M 5/32
[52] U.S. Cl. ................................ 604/198; 604/263; 604/110
[58] Field of Search ............... 604/187, 192, 194–198, 604/218, 263, 110; 128/919, 763–765

[56] References Cited

U.S. PATENT DOCUMENTS

| | | | |
|---|---|---|---|
| 2,571,653 | 10/1951 | Bastien . | |
| 3,780,734 | 12/1973 | Wulff . | |
| 3,890,971 | 6/1975 | Lesson et al. . | |
| 4,139,009 | 2/1979 | Alvarez . | |
| 4,356,822 | 11/1982 | Winstead-Hall . | |
| 4,425,120 | 1/1984 | Sampson et al. | 604/198 |
| 4,573,976 | 3/1986 | Sampson et al. | 604/198 |
| 4,631,057 | 12/1986 | Mitchell | 604/198 |
| 4,643,199 | 2/1987 | Jennings, Jr. et al. | 128/763 |
| 4,650,468 | 3/1987 | Jennings, Jr. | 604/110 |
| 4,655,751 | 4/1987 | Harbaugh | 604/198 |
| 4,666,435 | 5/1987 | Braginetz | 604/198 |
| 4,681,567 | 7/1987 | Masters et al. | 604/198 |
| 4,693,708 | 9/1987 | Wanderer et al. | 604/198 |
| 4,695,274 | 9/1987 | Fox | 604/198 |
| 4,702,738 | 10/1987 | Spencer | 604/198 |
| 4,723,943 | 2/1988 | Spencer | 604/198 |
| 4,731,059 | 3/1988 | Wanderer et al. | 604/192 |
| 4,737,144 | 4/1988 | Choksi | 604/198 |
| 4,743,233 | 5/1988 | Schneider | 604/192 |
| 4,758,231 | 7/1988 | Haber et al. | 604/198 |
| 4,772,272 | 9/1988 | McFarland | 604/198 |
| 4,782,841 | 11/1988 | Lopez | 128/164 |
| 4,790,828 | 12/1988 | Dombrowski et al. | 604/198 |
| 4,801,295 | 1/1989 | Spencer | 604/198 |
| 4,810,248 | 3/1989 | Masters et al. | 604/192 |
| 4,813,426 | 3/1989 | Haber et al. | 128/763 |
| 4,842,587 | 6/1989 | Poncy | 604/198 |
| 4,871,355 | 10/1989 | Kikkawa | 604/198 |
| 4,874,383 | 10/1989 | McNaughton | 604/198 |
| 4,923,445 | 5/1990 | Ryan | 605/195 |
| 4,927,018 | 5/1990 | Yang et al. | 206/365 |
| 4,929,237 | 5/1990 | Medway | 604/198 |
| 4,935,016 | 6/1990 | Deleo | 604/198 |
| 4,976,702 | 12/1990 | Andrews | 604/198 |
| 4,994,045 | 2/1991 | Ranford | 604/198 |
| 4,998,920 | 3/1991 | Johnson | 604/198 |
| 4,998,924 | 3/1991 | Ranford | 604/798 |
| 5,019,051 | 5/1991 | Hake | 604/198 |
| 5,024,616 | 6/1991 | Ogle, II | 604/192 |
| 5,024,660 | 6/1991 | McNaughton | 604/110 |
| 5,030,209 | 7/1991 | Wanderer et al. | 604/198 |
| 5,045,066 | 9/1991 | Scheuble et al. | 604/198 |
| 5,053,018 | 10/1991 | Talonn et al. | 604/198 |
| 5,057,086 | 10/1991 | Dillard et al. | 604/195 |
| 5,059,185 | 10/1991 | Ryan | 604/198 |
| 5,067,945 | 11/1991 | Ryan et al. | 604/198 |
| 5,088,988 | 2/1992 | Talonn et al. | 604/198 |

Primary Examiner—C. Fred Rosenbaum
Assistant Examiner—Mark O. Polutta
Attorney, Agent, or Firm—Andrew J. Beck; Montgomery W. Smith; Richard D. Allison

[57] ABSTRACT

A safety syringe of the type having a needle shield that is slidable between a needle exposing retracted position and a needle protecting extended position and wherein the needle shield is rotatable in the extended position to a locked and extended position. The safety syringe includes a collar mounted on the distal end of the syringe and a plurality of elongate keys on the interior surface of the needle shield. The keys are slidably received in various protrusions and slots on the collar to releasably retain the needle shield in the retracted and extended positions and to retain the needle shield in the locked and extended position. A needle sheath is also removably mounted on the distal end of the needle shield to cover the needle of the syringe when the needle shield is in the initial retracted position.

25 Claims, 7 Drawing Sheets

_Fig.16._

_Fig.17._

COMBINED SYRINGE AND NEEDLE SHIELD AND METHOD OF MANUFACTURE

This is a continuation-in-part of copending application Ser. No. 07/212,524 filed on Jun. 28, 1988 now U.S. Pat. No. 5,053,018.

This invention relates to syringes and, in particular, to a hypodermic syringe having a retractable needle guard primarily for the purpose of preventing accidental needle sticks.

Most syringes used today for medical or laboratory purposes are sold as disposable items intended to be used only once. Disposal of such syringes has posed a safety hazard for the individuals who use the syringes as well as for those who dispose of them. With the onset of AIDS, the concern for infection due to accidental needle sticks from used syringes has increased and a number of different devices have been proposed to minimize the possibility of spreading infectious disease due to accidents of this type.

One approach to this problem is to provide a retractable shield which, after the syringe has been used, can be pulled to an extended position where it covers the needle, making it difficult for an individual to accidentally contact the needle. A common feature of such constructions is that when the shield is pulled to its extended position, it is locked so that it cannot be retracted (thus exposing the needle) except by application of extraordinary force.

A number of such constructions have been proposed to satisfy the general requirement that the needle be permanently covered after the syringe has been used. Some of these constructions involve twist-to-lock mechanisms and, in others, locking occurs automatically when the shield is fully extended. These known devices satisfy many of the functional requirements of a needle shield but require, in most cases, modification of the standard syringe construction. This is highly undesirable for some manufacturers because of the sizable investment they may have already made in their existing molding equipment for producing the syringes.

Moreover, certain operational problems arise when a shield is incorporated into a syringe. For example, since the shield, when it is retracted, essentially covers the barrel of the syringe, it is desirable to be able to insert and remove a needle while holding onto the shield alone. This involves twisting and pushing (or pulling) the needle to place it on (or remove it from) the luer and can be awkward with some known constructions.

Further, constructions have been proposed which include an opening or slot in the side of the shield. This is undesirable because the needle can extend through the opening if the shield is deflected in the extended position.

Those devices which lock in response to axial movement 25 to the extended position, (i.e., without any rotation) have certain inherent drawbacks that result primarily from the requirement that substantial force be exerted axially to lock the shield in its extended position. In the first place, the likelihood of unintentional and irreversible locking is greater with such devices than with those devices which require rotation to lock. Also, it is difficult to verify that the shield is locked upon such forcible extension without attempting to retract the shield, which increases the possibility of unintended exposure of the needle. Finally, if the user's hand should slip from the shield while exerting the force necessary to extend the shield to the locked position, the user's hand may reflexively rebound back onto the needle point if the shield does not actually lock.

Other proposed devices have included open ended shields which would not block access to the needle point by small fingers.

Accordingly, it is an object of this invention to provide a protective shield of the type described which can be added at minimal expense to standard syringes.

Another object of the invention is to provide a relatively inexpensive protective shield which satisfies the functional requirements of a needle shield and includes none of the drawbacks mentioned above.

Another object is to provide an extendable needle shield for a syringe which performs all of the necessary functions of such a shield and which is particularly well suited to an automated process of manufacture.

A further object of the invention is to provide an extendable needle shield for a standard syringe which is improved both from the points of view of functional utility and cost of manufacture.

A still further object is to provide an inexpensive method of assembling a protective shield and syringe.

SUMMARY OF THE INVENTION

In accordance with the invention, a needle shield is mounted coaxially on a syringe barrel. The shield includes one or more elongated keys on its inner surface. A collar is provided on the forward end of the barrel. The collar may be a separate part or it may be integrally formed with the barrel and includes on its outer surface at least one locking slot. The key slides in a path outside of the locking slot and can be rotated into the locking slot when the shield is extended. Both the collar and shield can be molded from plastic materials so that the cost of the shield is relatively low.

In a preferred embodiment, the shield includes a plurality of elongated locking keys and the collar includes a plurality of locking slots. Each locking slot is defined by opposing walls, at least one of which includes a ramp over which the keys can ride when the shield is pulled to its extended position and rotated.

In the preferred embodiment, when the keys are rotated into the locking slots, rearward movement of the shield to its retracted position is prevented by a surface on the collar at the back of each locking slot. In accordance with a further feature of the invention, protrusions on the collar and the forward portions of the keys are shaped such that during assembly the keys are directed into keyways formed between the locking slots as the collar is moved relative to the shield. Thus, the construction is well suited to an automated process in which the collar and shield are secured to the syringe by machine.

Other benefits of the invention are set forth below in the detailed description which follows:

DETAILED DESCRIPTION

In its preferred embodiment, the invention is intended to be used in conjunction with a conventional syringe; however, a protective shield in accordance with the invention can be used for any medical or laboratory device having a needle, such as a blood collection tube holder with a double ended needle. Accordingly, as used herein, the term "syringe" is intended to include any medical or scientific device including a needle wherein it is desired to protect a user from accidental needle sticks.

In describing the invention, the "distal end" of a part refers to the end of the part closest to the needle point. The "proximal end" of a part refers to the end furthest from the needle point.

Figures 7, 8:
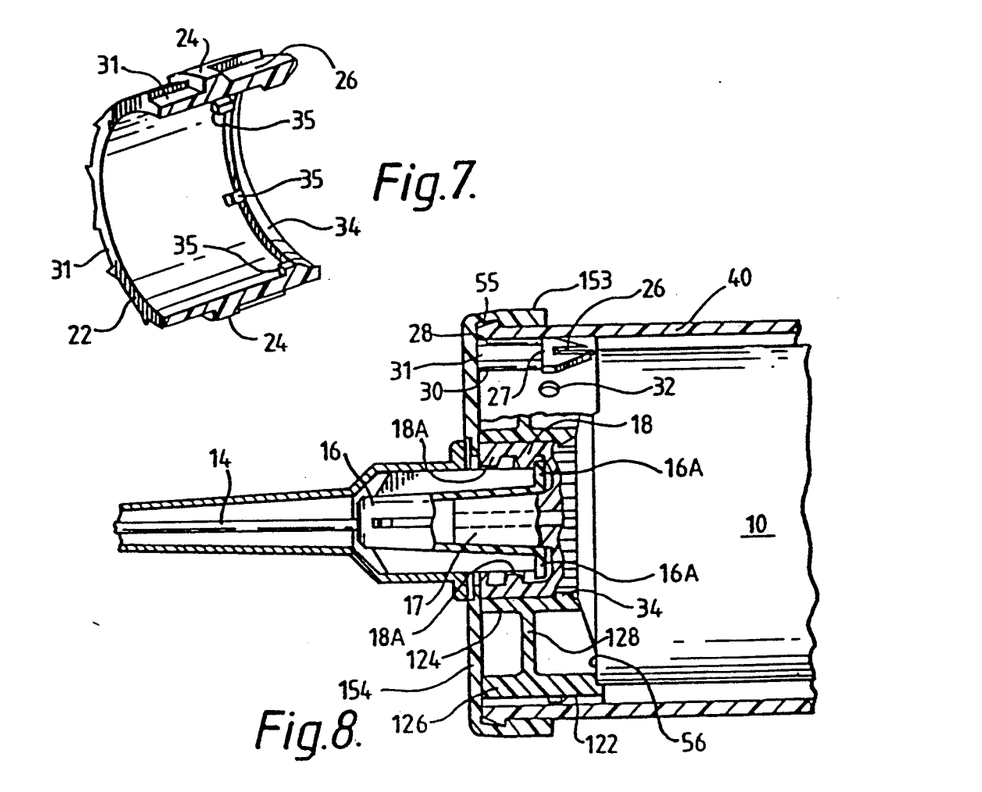
FIG. 8 is a side sectional view showing a collar construction for use with a large diameter barrel.

FIGS. 1-6 show a conventional syringe comprising a tubular barrel 10 having a finger flange 11, a plunger 12 slidable within the barrel 10, and a needle assembly through which the contents of the barrel are dispensed when the plunger 12 is depressed. The barrel 10 may be tapered very slightly (not shown) from a larger diameter proximal end to a smaller diameter distal end for molding purposes. The needle assembly comprises a needle 14 and a hub 16 at the proximal end of the needle. As is standard, a conically shaped luer tip 17 and luer lock skirt 18 are integrally formed at the distal end of barrel 10 with luer lock skirt 18 encircling luer tip 17. As shown in FIG. 8 (directed to a different collar construction and described in detail below), the interior surface of the luer lock skirt 18 includes an internal thread 18A adapted to threadably engage complementary locking ears 16A on the needle hub 16. The exterior surface of luer lock skirt 18 includes a multiplicity of ribs 19 parallel to the central axis of the barrel. The needle and luer arrangement of FIG. 8 is the same as that of FIGS. 1-6.

A needle sheath 20 covers needle 14 as a protective device. Sheath 20 frictionally engages hub 16 and can be used to disconnect the needle assembly from the luer lock skirt 18 in conventional fashion.

The construction as so far described is that of a standard disposable syringe and forms no part of the invention.

Figure 2:
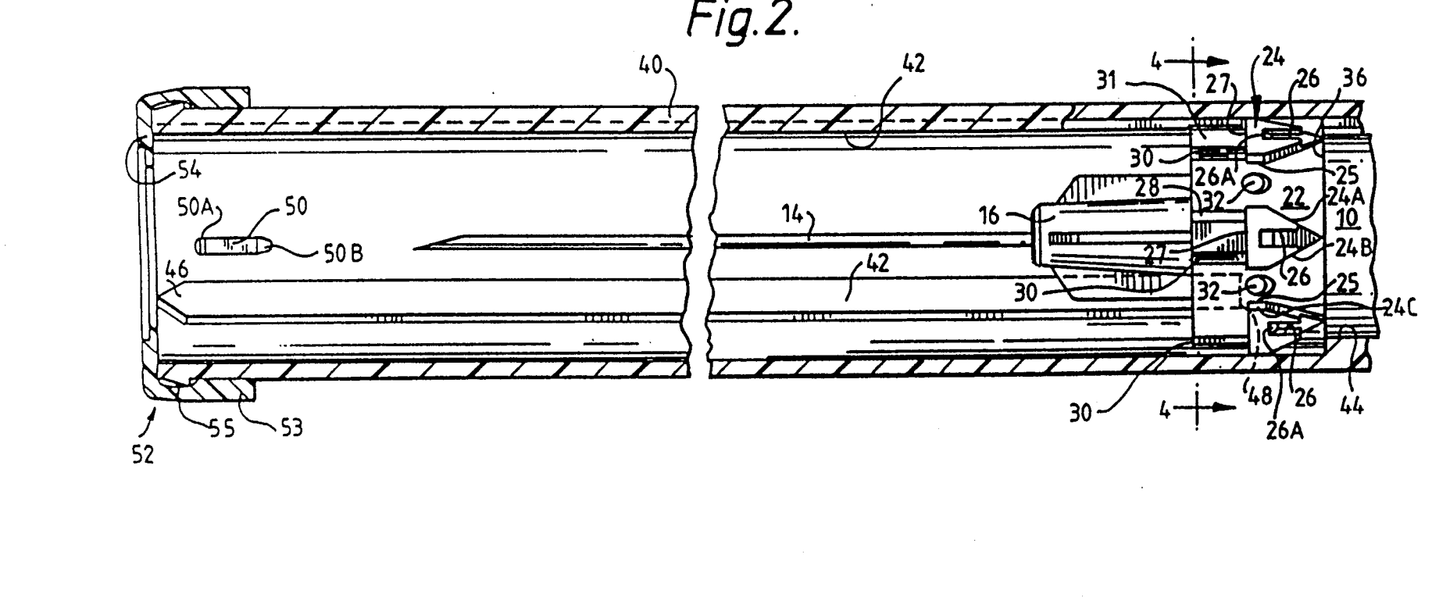
FIG. 2 is an enlarged sectional view with the shield in cross-section in its extended position.
Figures 5, 6:
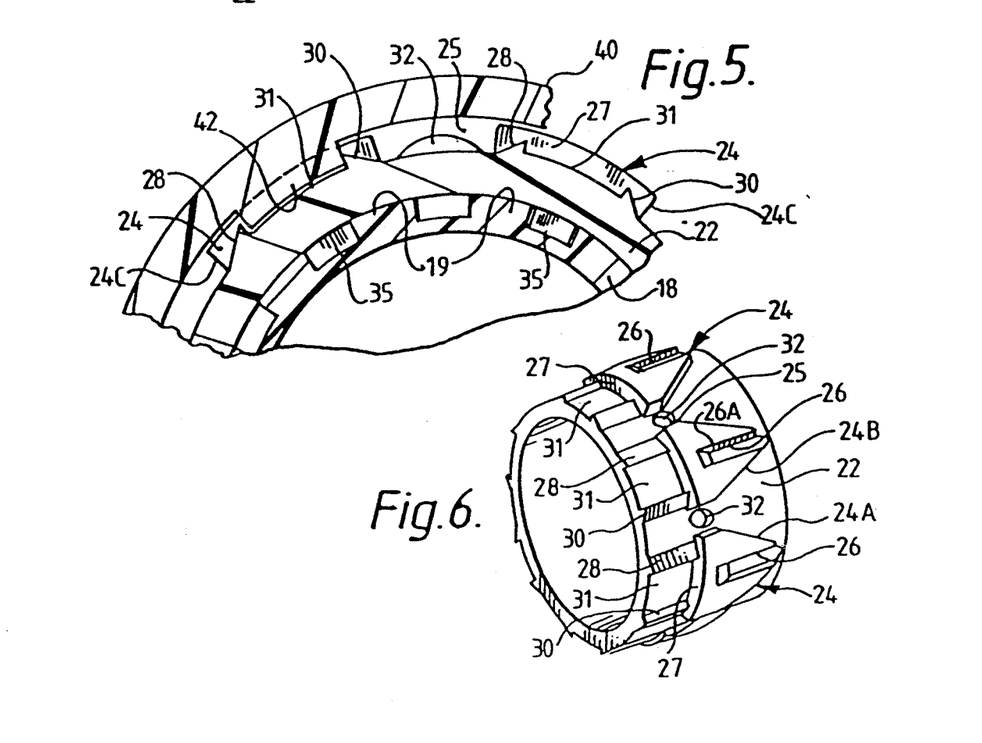
FIG. 5 is a sectional view along the line 4—4 of FIG. 2 showing the shield rotated into its locked position.
FIGS. 6 and 7 are perspective views of a preferred embodiment of the collar.

The collar employed in accordance with the preferred embodiment of the invention is shown generally at 22 (FIGS. 2, 6 and 8). As mentioned above, although collar 22 is shown as a separate piece, the collar (or its functional equivalent) may be integrally formed as a part of the barrel 10. It includes six equally spaced and integrally formed identical triangular protrusions 24, with the apex of each protrusion extending away from the needle. Keyways 25 are formed between each adjacent pair of protrusions 24.

The triangular protrusions 24 each include angled surfaces 24A and 24B, side surfaces 25C, a slot 26 and a surface 27 which is generally circumferential and functions as a stop as explained below. The slot 26 includes a sloped distal surface 26A. It is not necessary that protrusions 24 be triangular in shape and other configurations can be used to provide a stop 27 for the keys and the angled surfaces 25A and 25B necessary to guide the keys into the keyways during the assembly process as described below. The slot 26 is formed in protrusion 24 and extends proximally to the point of the protrusion 24 to expose the detenting surface 26A and facilitate the entry of the detent 50 into the slot 26 during assembly, and also to facilitate efficient molding of the collar. At the forward end of each protrusion, two walls 28 and 30 extend toward the needle. A rectangular locking slot 31 is formed between each pair of walls 28 and 30, which are ramp shaped in cross section as shown most clearly in FIGS. 4, 5 and 6. As shown in FIGS. 3, 4, 5 and 6, the surface of locking slot 31 is slightly elevated relative to the level of the keyways 25, i.e., the collar diameter at the locking slots 31 is slightly greater than the collar diameter at the keyways. The slight increase in the collar diameter at the locking slots removes some of the slack between the needle shield (described below) and the collar 22 resulting from the slight taper of the barrel 10 in the preferred embodiment. This prevents or at least minimizes the wobble or play of the shield about the collar 22 when it is locked in the extended position. A circular detent 32 is positioned between each pair of triangular protrusions 24 with the forward points of detents 32 lying just in front of the bases of triangular projections 24.

Figure 3:
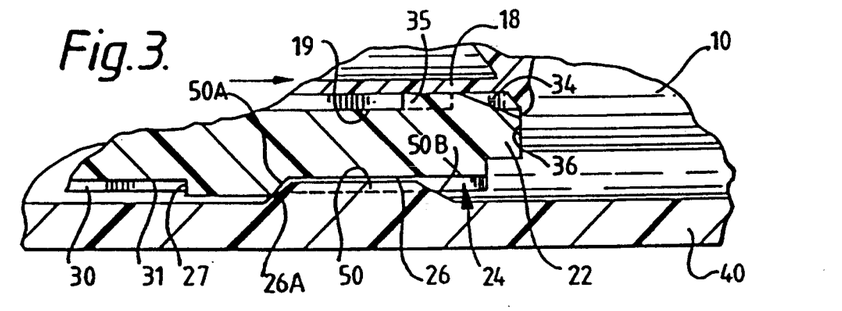
FIG. 3 is a further enlarged partial side sectional view showing details of the collar and shield.
Figure 4:
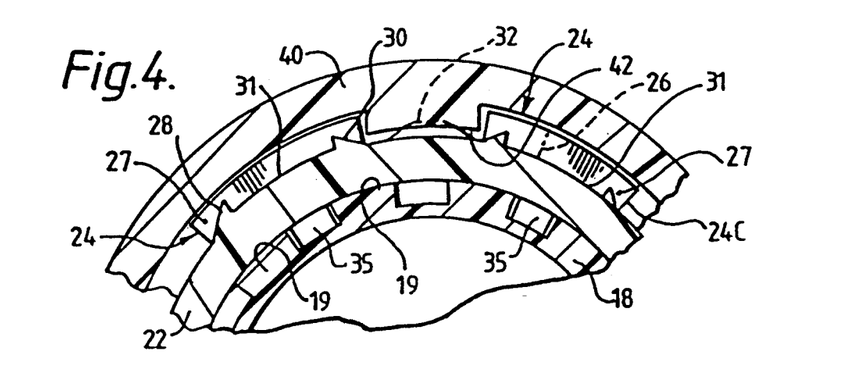
FIG. 4 is a sectional view along the line 4—4 of FIG. 2 with the shield pulled to its extended position but before rotation.

As shown most clearly in FIG. 3, the rear end of collar 22 includes a peripheral rigid tooth 34 adapted to engage the ribs 19 in the luer lock skirt 18 to retain the collar 22 on the syringe. Collar 22 is molded of a rigid plastic material such as polycarbonate resin so that when the collar is pushed over the luer lock skirt 18, the angled surface of the rigid tooth 34 allows the tooth to move over the ribs 19 until the proximal end of the collar is seated toward the distal end of the barrel with the rigid tooth 34 deforming the ribs 19 of the luer lock skirt 18 to permanently retain the collar in place on the syringe barrel 10. As an alternative, a circumferential groove may be formed in collar 22 to receive the peripheral tooth 34. This is unnecessary in the preferred embodiment in which the yieldable ribs 19 cold flow into the configuration shown in FIG. 3 but may be desirable in the case of syringes which do not include ribs molded on the exterior surface of the luer lock skirt. Instead of mechanically interlocking the collar 22 and barrel 10, other fastening means such as sonic welding or adhesives may be used within the scope of the invention, although such techniques are generally disadvantageous because of the additional steps involved and other problems which may arise with the preferred assembly techniques. The diameter of collar 22 as measured in the area of the keyways 25 is greater than the outer diameter of the syringe barrel 10 adjacent the collar.

Locking lip 34 will bite sufficiently into the outer surface of the luer skirt 18 to prevent axial movement of collar 22 but in some cases slight rotation or rocking of the collar may occur. To prevent this, the tooth 34 may be formed with gaps (not shown) so that not all of the ribs 19 on the outside of the luer lock skirt 18 will be deformed. The non-deformed ribs 19 falling into the gaps resist rotation or rocking of the collar 22 relative to barrel 10. Alternatively, as shown in FIGS. 3 and 7, the inner surface of collar 22 may be provided with lugs 35 molded on the inside of the collar and adapted to fit between the ribs 19 on the outside of the luer lock skirt 18 to prevent positively any rotational movement with the meshed ribs 19.

The needle shield comprises an elongated plastic cylinder 40 (e.g., made of polypropylene) having three keys 42 integrally formed on its interior surface. An end rim 44 is formed at the proximal end of shield 40. As shown in FIG. 2, end rim 44 is adapted to abut against the proximal end of collar 22 to limit the forward movement of the shield. Each of the keys 42 includes a distal triangular point 46 and extends from the distal end of the shield to a point just short of the distal point of the triangular protrusions 24 on collar 22 when the shield is in its extended position as shown in FIG. 2. End rim 44 includes three cutout sections 45 which align with each of the keys 42. Cutout sections 45 facilitate the process for molding keys 42 but serve no functional purpose after the device has been assembled. At their rear ends, the keys 42 terminate in flat surfaces 48. With the three keys 42 in the keyways 25 in the retracted position (FIG. 1), rotational movement of the shield 40 is prevented by abutment of the edges of keys 42 against the side surfaces 24C of protrusions 24; therefore, torque can be applied to the needle while holding shield 40 to thread (or unthread) needles onto (or from) the syringe. This cannot be done with constructions in which a shield rotates freely with respect to the syringe.

Figure 1:
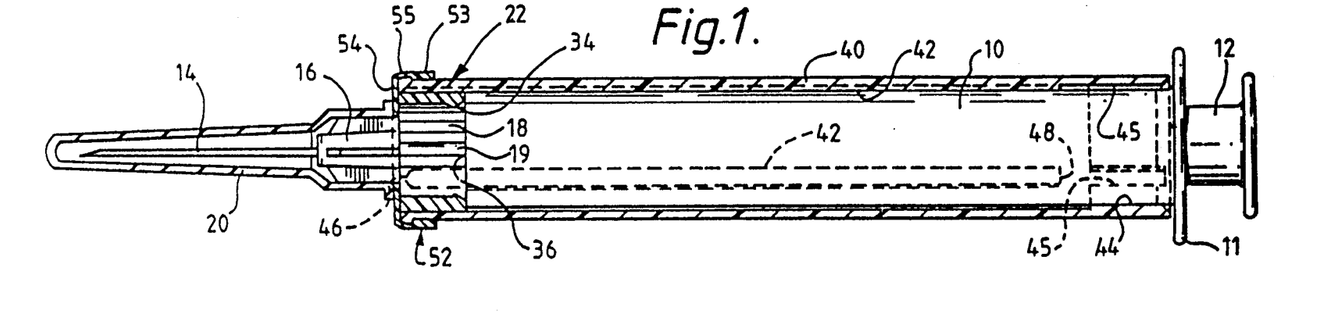
FIG. 1 is a side elevational view, partly in section, showing a needle shield and collar in accordance with a preferred embodiment of the invention secured to a conventional syringe with the shield in its retracted position.

Three detents 50 are also formed on the inner surface of the shield 40 toward its forward end. The detents 50 may be equally spaced and are adapted to be received within the slots 26 in the triangular protrusions 24 to retain the shield 40 in its retracted position (FIG. 1). In the preferred embodiment, as shown in the drawings, the detents 50 are each spaced thirty degrees from an adjacent key 42. It is not necessary that the detents be equally spaced. Each of the detents includes a sloped distal surface 50A and a proximal surface 50B more gradually sloped than slope 50A.

In the retracted position, the distal end of shield 40 terminates at the same point as the distal end of collar 22. An end cap 52 (see FIG. 2) is placed on the forward end of the shield 40. Cap 52 is molded from a resilient plastic material (such as polyallomer) and includes a side wall 53 and an end wall 54 which is adapted to be positioned between the distal end of collar 22 and the proximal end of the needle sheath 20 (FIG. 1) for substantially closing the distal end of shield 40. Side wall 53 is shaped as shown so that end cap 52 can be retained on shield 40 by the interlocking mechanical engagement of the side wall 53 and a complementary projection 55 at the forward end of shield 40. Cap 52 need not be a separate part and can, instead, be formed as an integral part of shield 40.

The end wall 54 includes a central needle aperture which is made small enough that the end of shield 40 is closed to the maximum extent while allowing the locking ears 16A of needle hub 16 to be extended through the aperture to permit needles to be mounted and removed while the shield 40 is in its retracted position (FIG. 8). The aperture is not, however, large enough to allow the proximal end of the sheath to pass through it. The minimum needle aperture reduces the likelihood that a child or person with small fingers may accidentally contact the needle point. End cap 52 also makes the distal end of shield 40 more rigid and resistive to deformation when dropped or otherwise impacted upon a hard surface.

In addition, the rim 54 and its position between the proximal end of needle sheath 20 and the distal end of barrel serves a functional purpose when removing or installing needles on the luer tip 17 (FIG. 8), for example, when the filling and injection needles are different. When a needle is to be mounted on a syringe, the syringe is held by shield 40 with the shield in its retracted position. Needle hub 16, projecting from the proximal end of the protective sheath 20, is inserted through the aperture in the end wall 54 and the hub telescoped onto the luer tip 17. Using the conventional cooperative wrenching tabs (not numbered) of the sheath and needle, the needle hub 16 is rotated by twisting and pushing with the sheath to thread the locking tabs 16A within the internal threads 18A in the luer skirt 18 until needle 14 is mounted on the syringe. As hub 16 is threaded onto the luer tip 17, the needles move axially relative to sheath 20. The shield 40 is prevented from rotating by abutment of keys 42 against surfaces 24C of protrusions 26, while the rim 54 provides a surface against which the needle sheath can be forced. Without this feature, the user could not grasp the shield alone when installing and removing the needle since the force exerted by the needle hub on the syringe luer tip would push the syringe out of the shield. This would mean that the user would have to remember to grasp the barrel and not the shield when removing or attaching the needle.

Figure 9:
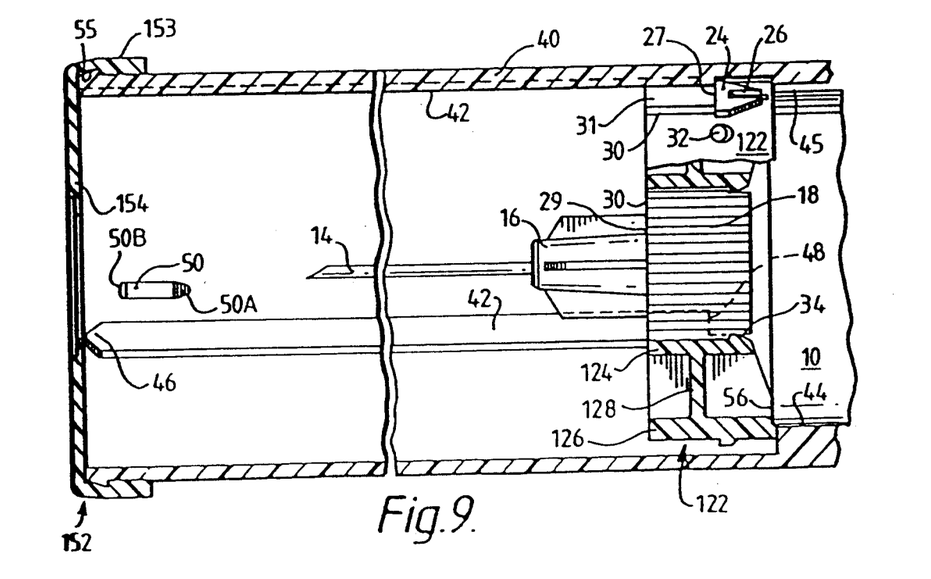
FIG. 9 is an enlarged side sectional view showing a shield in its extended position relative to the collar of FIG. 8.

The end wall 54 is particularly important when the invention is used in conjunction with large diameter barrels. Such a construction is shown in FIGS. 8 and 9 wherein like numerals are used to identify parts identical to those shown in the embodiment of FIGS. 1–6. In FIGS. as is the luer tip 17 and the luer lock skirt 18. In this case, however, the collar 122 includes two concentric hubs or sleeves 124 and 126 supported by an annular strut 128 preferably forming an I-beam in cross-section as shown in FIG. 9. The cross-sectional shape is not critical, however, and those skilled in the art will readily understand that the cross-section could be cupor channel shaped, with a web extending either distally or proximally between the concentric hubs or sleeves. The end cap 152 includes side wall 153 and end wall 154 which, as shown, covers a substantial portion of the barrel opening and thus greatly reduces the risk of accidental needle stick when the shield is in its extended position.

The device may be assembled as follows. Shield 40 is inserted on the forward end of the barrel 10 of an assembled syringe to its retracted position shown in FIG. 1 (prior to installation of the needle 14 and sheath 20 on the syringe). With the shield 40 held in position, the collar 22 is then placed over the luer lock skirt 18 inside of the shield 40. Engagement of the triangular protrusions 24 on collar 22 with the triangular points 46 at the end of keys 42 on shield 40, as the collar 22 is pushed onto the luer lock skirt 18, causes the shield 40 to rotate until the keys 42 are positioned in the keyways over detents 32 between adjacent triangular protrusions 24. The collar 22 is pushed inwardly until the proximal end of the collar butts up against the face 56 on the syringe barrel 10. In this position, as shown in FIG. 3, the three detents 50 are seated in the slots 26 of three of the protrusions 24. After the shield 40 and collar 22 have been assembled on the syringe, end cap 52 is placed on the shield 40. The needle 14 with its sheath 20 may then be attached to the luer tip to complete the assembly.

Alternatively, collar 22 may be positioned within shield 40 with the keys 42 positioned in the appropriate keyways 25. The shield and collar may then be telescoped together over the syringe barrel with the collar being forced onto the luer lock skirt as the shield is moved to the retracted position in which the proximal end of the collar abuts against the distal face of the syringe barrel. This procedure, with appropriate tooling, may be used with the end cap 52 in place on the shield which means that this assembly process could be used with a shield having end wall 54 integrally formed as a portion of the shield as mentioned above. Conversely, this alternative assembly method can be used with an open shield in which case end cap 52 can be placed on the shield after assembly.

The use of the syringe may be conventional. Needle sheath 20 is removed and medication drawn into barrel 10 by withdrawal of plunger 12 with the shield in its retracted position shown in FIG. 1. After the contents of the syringe have been injected into a patient, the shield 40 is pulled forward into the extended position shown in FIG. 2. When this happens, the keys 42 slide in the keyways 25 over detents 32 between the adjacent protrusions 24 on collar 22 (FIG. 4) and the distal surfaces 50A of detents 50 slide over surfaces 26A (FIG. 2) of slots 26. The user can feel the rear edges 48 of keys 42 clearing detents 32, which signals that the shield 40 is fully extended.

To lock the shield in place, the user rotates shield 40 causing the keys 42 to move over the adjacent ramps 28 (or 30) until the keys fall into the locking slots 31 formed between each pair of ramps 28 and 30 (see FIG. 5). Because of the arrangement of the ramps 28 and 30, the shield can be locked by rotating it either clockwise or counterclockwise. When the keys 42 are positioned in the locking slots 31, the rear edge 48 of each key abuts against the squared off surface 27 of one of the triangular protrusions 24 so that the shield cannot be returned to its retracted position without application of excessive force. Because of the interlocking relationship of the square key and locking slots, shield 40 can no longer be rotated and, accordingly, the shield is permanently locked in place.

There are circumstances where it may be desirable to extend the shield 40 to the position shown in FIG. 2 without locking it in place. For example, if a syringe is to be filled at a location remote from the patient, rather than replacing the sheath 20 after the syringe is filled, it is preferable to extend shield 40 so that it functions as a temporary protective element while the syringe is carried to the patient. Use of the protective shield 40 in this fashion is facilitated by the detents 32 on collar 22. These detents 32 are positioned in each of the keyways 25 between the triangular protrusions 24 so that when the shield 40 is pulled to its extended position (FIG. 2), the flat end 48 of each of the keys 42 abut against one of the detents 32. This prevents the shield 40, when it is in its extended position, from being retracted unless sufficient force is applied to move the keys 42 over the detents 32. Hence, in this situation, the shield is first extended as a temporary sheath for the needle, returned to its retracted position for the patient's injection, and then finally again extended and locked by rotation so that the shield cannot be retracted. If it is desired to return the shield 40 to its retracted position rather than locking the shield in its extended position, because of the gradual slope of surface 50B of detent 50, the detent can be pushed over the squared off surface 27.

FIGS. 10-17 illustrate a further embodiment of the present invention wherein the collar and shield are modified for use on a syringe having a needle integrally molded on the distal end thereof. As described hereinafter, this embodiment of the present invention is particularly useful with relatively small diameter syringes such as a 1 cc insulin syringe.

The collar employed in accordance with the present embodiment is shown generally at 222. As mentioned previously, although the collar 222 is shown as a separate piece, the collar (or its functional equivalent) may be integrally formed as part of the distal end of the syringe barrel 210. The collar 222 includes four equally spaced and integrally formed triangular protrusions 224, with the apex of each protrusion 224 extending proximally away from the needle. Keyways 225 are formed as recesses between each adjacent pair of protrusions 224.

The triangular protrusions 224 on the outer surface of the collar 222 each include angled surfaces 224A and 224B, side surfaces 225C, a slot 226 and a surface 227 which is generally circumferential and functions as a stop for the proximal end of the key 224 as explained hereinafter. The slots 226 on the protrusions 224 includes a sloped distal surface 226A. Although it is not necessary that the protrusions 224 be triangular in shape, it is anticipated that other configurations may be used to provide a stop surface 227 for the keys 242 (as described hereinafter) and the angled surfaces 225A and 225B may be modified as necessary to guide the keys 242 through the keyways 225 as described hereinafter. The slot 226 is formed in each protrusion 224 and extends proximally from an angled detenting surface 226A to the triangular point of the protrusion 224. At the forward or distal end of each protrusion 224, two ramp shaped wall members 228 and 230 extend longitudinally along the outer surface of the collar 222 toward the needle. A rectangular locking slot 231 is formed between each pair of wall members 228 and 230 as shown most clearly in FIG. 14. The surface of the locking slot 231 is slightly elevated relative to the level of the keyways 225, i.e. the collar diameter at the locking slots 231 is slightly greater than the collar diameter at the keyways 225. This slight increase in the collar diameter at the locking slots 231 removes some of the slack between the needle shield 240 and the collar 222 caused by the slight taper of the distal end of the barrel 210. This prevents or at least minimizes the wobble or play of the shield 242 when it is locked in the extended position as described hereinafter. A raised spherical detent 232 is positioned between each pair of triangular protrusions 224 with the distal portion of the spherical detent 232 being located slightly distal to the stop surface 227 of the triangular protrusion 224 and the proximal portion of the spherical detent 232 being located between the side surfaces 225C of the protrusions 224.

Figure 11:
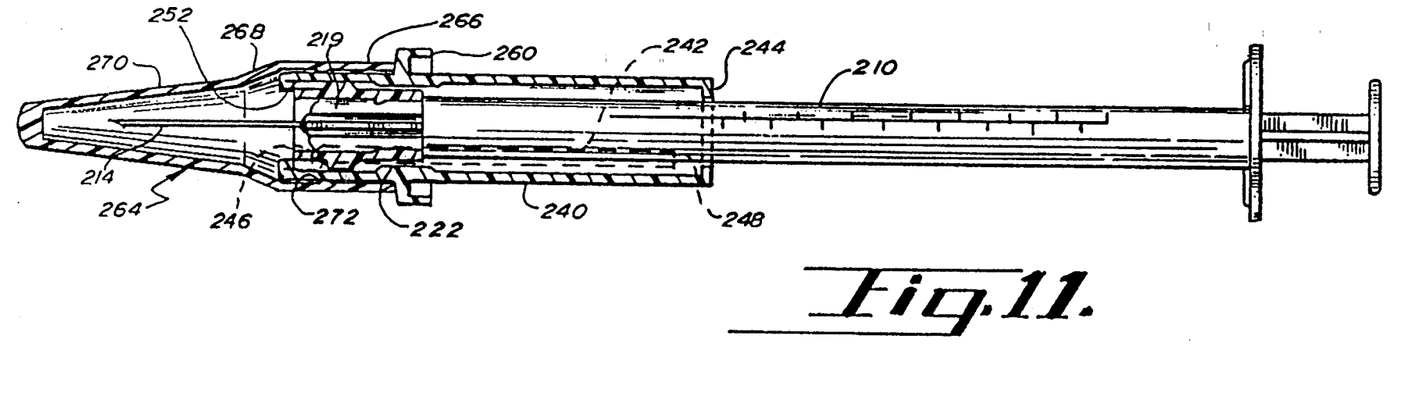
FIG. 11 is a side view partially in cross-section, showing the needle shield, collar and needle sheath of the embodiment shown in FIG. 10 in the retracted position and mounted on a syringe.
Figure 12:
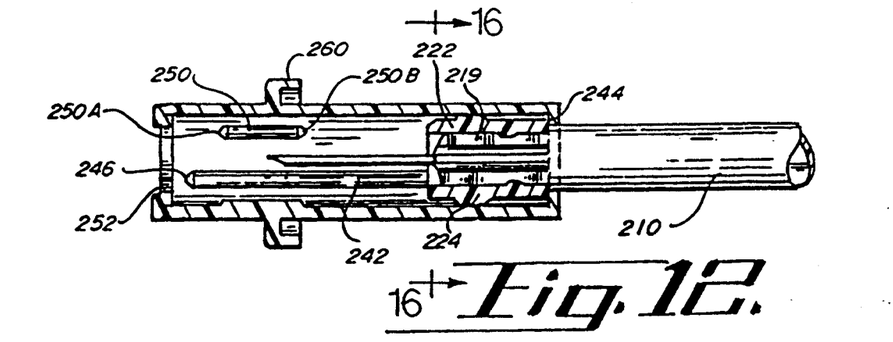
FIG. 12 is a side view partially in cross-section, showing the needle shield of the embodiment shown in FIG. 10 in the extended position.

As shown most clearly in FIGS. 11 and 12, the proximal portion of the interior surface of the collar 222 includes an inwardly extending annular rigid tooth 234 which is adapted to engage the ribs 219 on the distal end of the syringe to retain the collar 222 on the syringe. Additionally, a plurality of longitudinally oriented stop ribs 235 are located on the interior proximal portion of the collar 222 between the rigid tooth 234 and the proximal end of the collar 222. The collar 222 is molded of a rigid plastic material such as a polycarbonate resin so that when the collar is pushed over the distal end of the syringe, the angled surface of the rigid tooth 234 allows the tooth 234 to move over the ribs 219 until the proximal end of the collar 222 is securely seated against the distal end of the barrel 210 with the rigid tooth 134 slightly deforming the ribs 219 of the distal end of the syringe to permanently retain the collar 222 in place on the syringe. As described above, the rigid tooth 234 will bite sufficiently into the outer surface of the distal end of the syringe to prevent axial movement of the collar 222 along the syringe. In some cases slight rotation of the collar 222 may occur and therefore, a plurality of stop ribs 235 are formed on the interior surface of the proximal end of the collar 222 so that the ribs 219 on the distal end of the syringe will fall into gaps between the stop ribs 235 to resist rotation of the collar 222 relative to the barrel 210. The combination of the rigid tooth 234 and the stop ribs 235 provides an adequate mechanical interlocking of the collar 222 onto the distal end of the syringe. It is anticipated that other fastening means such as sonic welding or adhesives may be used within the scope of the present invention, although such techniques are generally disadvantageous because of the additional steps involved and other problems which may arise during assembly of the present embodiment.

The needle shield 240 of the present embodiment preferably comprises an elongated plastic cylinder made of a semirigid material such as polypropylene. As shown in the drawings, the needle shield of this embodiment preferably has two longitudinally oriented keys 242 integrally formed along its interior surface. A proximal end rim 244 is formed at the proximal end of the shield 240. As shown in FIG. 12, the proximal end rim 244 is adapted to abut against the proximal end of the collar 222 to prevent the forward or distal movement of the shield 240 beyond the extended position as described hereinafter. Each key 242 includes a triangularly shaped distal end 246 and extends longitudinally along the shield 240 from a location adjacent to the distal end of the shield 240 to a proximal end 248 located adjacent to the distal point of the triangular protrusions 224 on the collar 222 when the shield 240 is in its extended position as shown in FIG. 12. The proximal end rim 244 includes a pair of cut-out sections which are aligned with each of the keys 242 to facilitate the process for molding the keys 242 on the interior surface of the needle shield 240. As shown in phantom in FIG. 11, the proximal end 248 of the keys 242 terminate in slightly rounded surfaces. The keys 242 also include a slightly recessed longitudinal groove 249 which extends substantially along the keys 242 between the triangular distal end 246 (FIG. 12) and the rounded proximal end 248 of the keys 242 to facilitate the sliding movement of the spherical detent 232 therein as the needle shield 240 is moved between the retracted and extended positions. With the two keys 242 in the keyways 225 on the collar 222, rotational movement of the shield 240 is prevented by the abutment of the edges of the keys 242 against the side surfaces 225C of the protrusion 224 so that the needle shield 240 will not rotate about the syringe barrel 210 as the needle shield 240 is moved between the retracted and extended positions.

Figure 13:
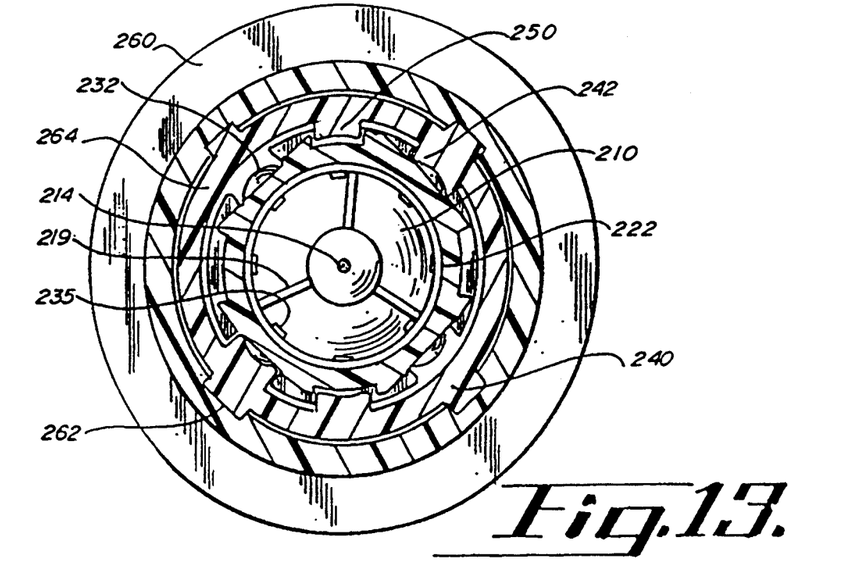
FIG. 13 is a cross-sectional view of the needle shield and needle sheath of the embodiment shown in FIG. 10 taken generally along lines 13—13 of FIG. 10.
Figure 14:
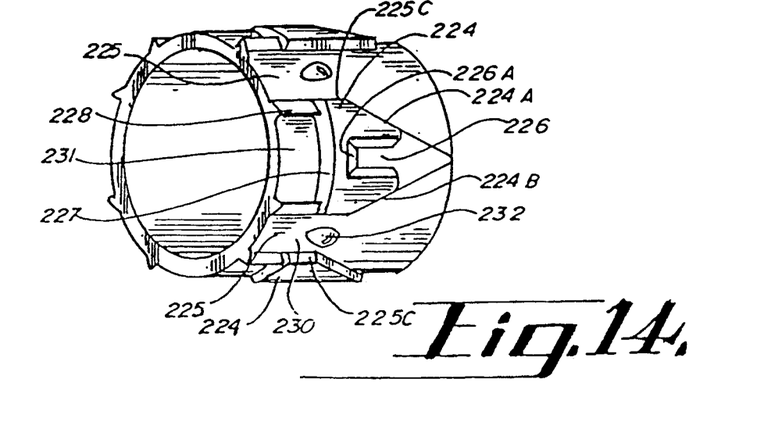
FIG. 14 is an elevated perspective view of the collar of the alternate embodiment as shown in FIG. 11.
Figure 15:
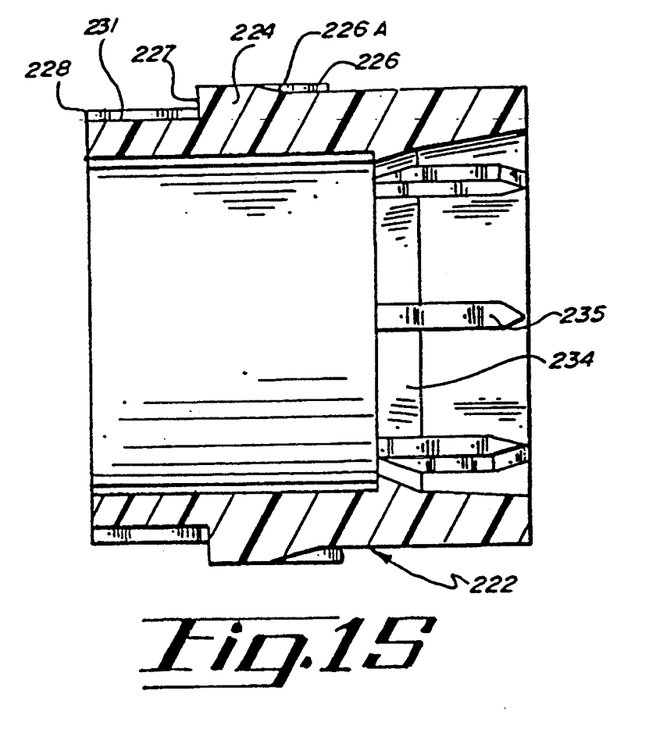
FIG. 15 is a cross-sectional view of the collar shown in FIG. 14 showing a cross-sectional view through the protrusions and locking slots of the collar.
Figure 16:
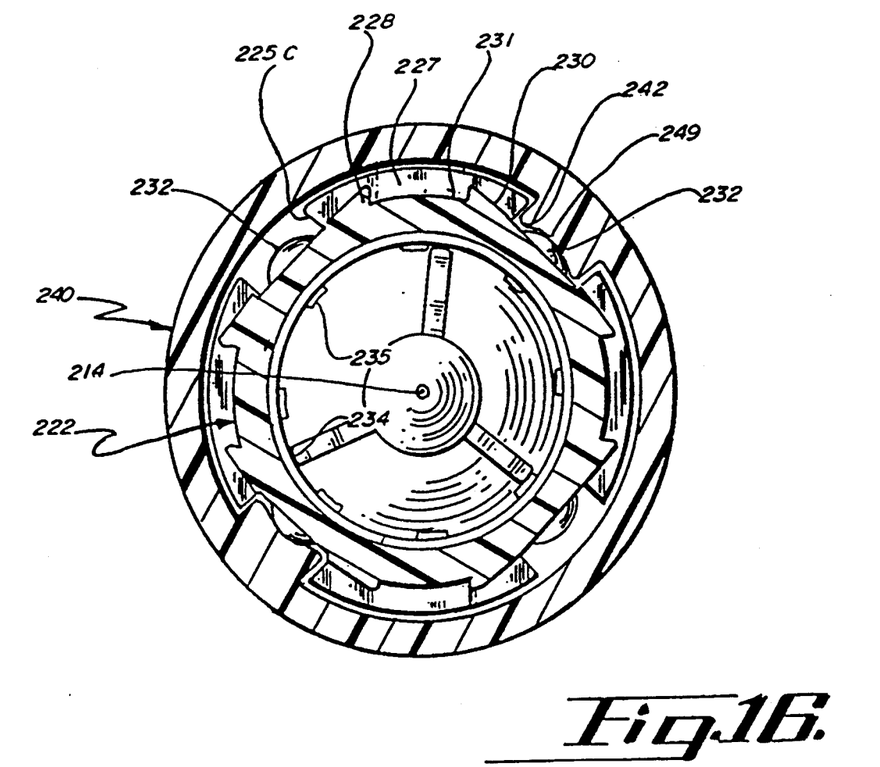
FIG. 16 is a cross-sectional view taken generally along lines 16—16 of FIG. 12 showing the collar and needle shield of the present embodiment in the extended and unlocked position.

As shown in FIGS. 12 and 13, a pair of longitudinal detents 250 are formed on the inner surface of the needle shield 240 near the distal end of the needle shield 240 and keys 242. These longitudinal detents 250 are radially spaced apart from the keys 242 and are adapted to be received within the slots 226 on the protrusions 224 to prevent the needle shield 240 from freely sliding along the collar 222 when the needle shield 240 is in the retracted position. In the present embodiment, the longitudinal detents 250 are each spaced approximately 45. from an adjacent key 242 and are positioned to be received in the slots 226 of the protrusions 224 when the needle shield 240 is in the retracted position as described above. The longitudinal detents 250 each include a sloped distal end 250A and a proximal end 250B which has a more gradually sloped surface than the surface of the distal end 250A. When the needle shield 240 is in the retracted position, as shown in FIG. 11, the distal end 250A of each detent 250 contacts the angled detenting surface 226A at the distal end of the slots 226 on the collar 222. The contact between the distal end 250A of the detent 250 and the angled detenting surface 226A creates a slight resistance to the movement of the needle shield 240 from the retracted position to the extended position. The contact between the gradual slope of the proximal end 250B of the detent 250 and the angled detenting surface 226A provides a gradual increase in resistance as the needle shield 240 is moved from the extended position to the retracted position. This contact provides a distinct click or release of tension as the detent 250 passes through the locking slot 231 and over the distal portion of the protrusion 224 and into slot 226 as the needle shield 240 reaches the fully retracted position. As shown in FIG. 11, a distal end cap 252 is formed on the distal end of the needle shield 240 by inwardly folding a portion of the distal end of the needle shield 240. The distal end cap 252 limits the proximal travel of the needle shield 240 along the barrel 210 so that the distal end of the needle shield 240 is adjacent to the distal end of the collar 222 when the needle shield 240 is in the retracted position.

Figure 10:
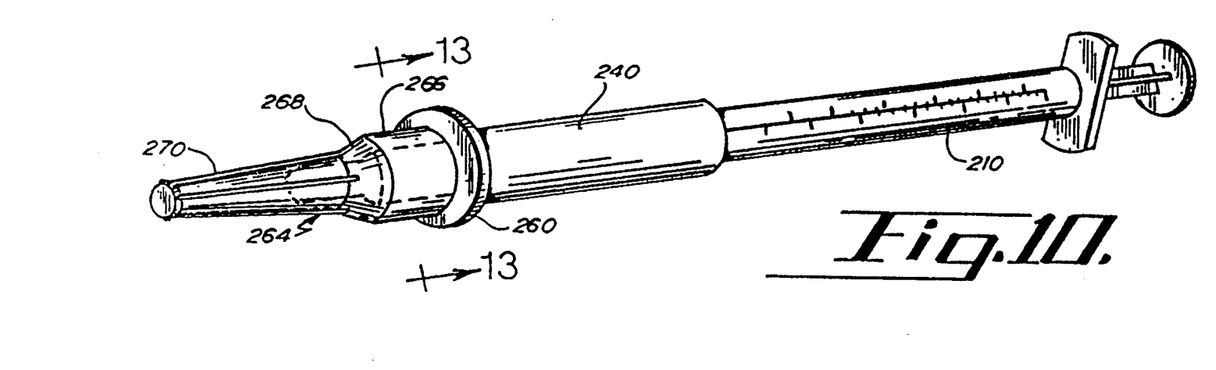
FIG. 10 is an elevated perspective view of an alternate embodiment of the present invention showing the needle shield and needle sheath of the alternate embodiment in the retracted position.

As shown in FIG. 10, the outer surface of the needle shield 240 includes a radially extending finger flange 260. In the preferred form of the present embodiment, the finger flange 260 is spaced from the distal end of the needle shield 240 approximately 1/5 of the length of the needle shield 240. Because the prevent embodiment is designed primarily for use on relatively small diameter syringes, the finger flange 260 adds further protection for the user by providing a radially extending surface which may be grasped by the user to move the needle shield 240 between the extended and retracted positions without having the user's hands unnecessarily close to the needle. The outer surface of the distal end of the needle shield 240 also includes four equally spaced and longitudinally aligned ridge members 262 (FIG. 13). These ridge members 262 extend between the distal end of the needle shield 240 and the finger flange 260 to provide a contact surface for the interior of the needle sheath 264 as described hereinafter.

As shown in FIGS. 10 and 11, the needle sheath 264 is a generally closed cylindrical member having an open proximal portion 266; a tapered intermediate portion 268 and a reduced diameter distal section 270 having a closed end thereon. The interior surface of the proximal portion 268 of the needle sheath 264 includes an inwardly extending annular rib 272 which is designed to contact and deform the ridge members 262 on the exterior surface of the distal end of the needle shield 240. The needle sheath 264 of the present invention is designed to be frictionally mounted on the exterior surface of the distal end of the needle sheath 240. Additionally, the needle sheath 264 may be further heat staked to the distal end of the needle shield 240 to provide further retention of the needle sheath 264 on the needle shield 240. The assembly of the present embodiment may be accomplished in the same manner as described above with respect to the preferred embodiment with the additional steps of attaching the needle sheath 264 to the needle shield 240 after the needle shield 240 and collar 222 have been assembled on the syringe and crimping the distal end of the needle shield 240 to form the distal end cap 252 on the distal end of the needle shield 240.

The use of the present embodiment provides a further advantage over the above-described preferred embodiment by enabling the user to move the needle shield 240 to the extended position prior to removing the needle sheath 264 from the distal end of the needle shield 240. This allows the user to remove the needle sheath 264 from the present embodiment while the needle 214 remains protected by the needle shield 240.

The present embodiment also allows the user to safely resheath the syringe once the syringe has been filled with the desired medication. When the user desires to transport the medication-containing syringe from the filling area to the patient, the needle shield 240 may be moved to the releasable extended position and the needle sheath 264 may be returned to the distal end of the needle shield 240 to provide further protection against accidental contact with the needle 214. By allowing the user to position the needle sheath 264 on the needle shield 240 when the needle shield 240 is in the releasable extended position, it is not necessary for the user to place their fingers unacceptably close to the needle 214 during the resheathing process. Additionally, by resheathing the needle 214 while the needle shield 240 is in the extended position, the needle point will not be accidentally damaged by contact with the needle sheath 264.

When the present embodiment is in the retracted position as shown in FIGS. 10 and 11, the needle shield 240 is generally axially aligned along the barrel 210 of the syringe and extends approximately one-half of the distance of the barrel 210. The distal end of the needle shield 240 is adjacent to the distal end of the collar 222 so that the distal end cap 252 of the needle shield 240 contacts the distal end of the collar 222 to prevent further proximal movement of the needle shield 240 along the barrel 210. In this position, the distal ends 250A of the longitudinal detents 250 contact the angled detenting surfaces 226A in the slots 226 on the collar 222. The triangular distal end 246 of the keys 242 extend slightly beyond the spherical detents 232 so that the spherical detents 232 are aligned in the distal portion of the longitudinal groove 249 adjacent to the distal end 246 of each of the keys 242. The needle sheath 264 extends from the distal end of the needle shield 240 to protect and entirely enclose the needle 214 which is permanently attached to the distal end of the syringe.

As the needle shield 240 is moved from the retracted position to the extended position, the longitudinal detents 250 on the needle shield 240 are initially forced over the angled detenting surfaces 226A in the slots 226 on the collar 222 and the keys 242 slide along the keyways 225 on the collar 222 so that two of the spherical detents 232 on the collar 222 will slide longitudinally in the longitudinal grooves 249 in the keys 242 and so that the longitudinal detents 250 are released from contact with the collar 222 as the needle shield 240 is initially moved from the retracted position.

When the needle shield 240 reaches the extended position, the spherical detents 232 pass from the longitudinal grooves 249 in the keys 242 and into contact with the proximal end 248 of each key 242. The proximal end 248 of the keys 242 are shaped so that as the proximal ends 248 of the keys 242 passes beyond the distal surface of the spherical detents 232 on the collar 222, the user feels and hears an audible click as the needle shield 240 reaches the fully extended position. Additionally, in the fully extended position, the proximal end rim 244 of the needle shield 240 contacts the proximal end of the collar 222 so that further distal movement of the needle shield 240 is prevented. Next, if the user has not previously done so, the needle sheath 264 may be removed from the distal end of the needle shield 240. If the user so desires, they may then return the needle shield 240 to the retracted position by sliding the needle shield 240 proximally and linearly along the syringe barrel 210 so that the longitudinal detents 250 pass over the protrusions 224 and into the slots 226 to releaseably retain the needle shield 240 in the retracted position as described above.

Figure 17:
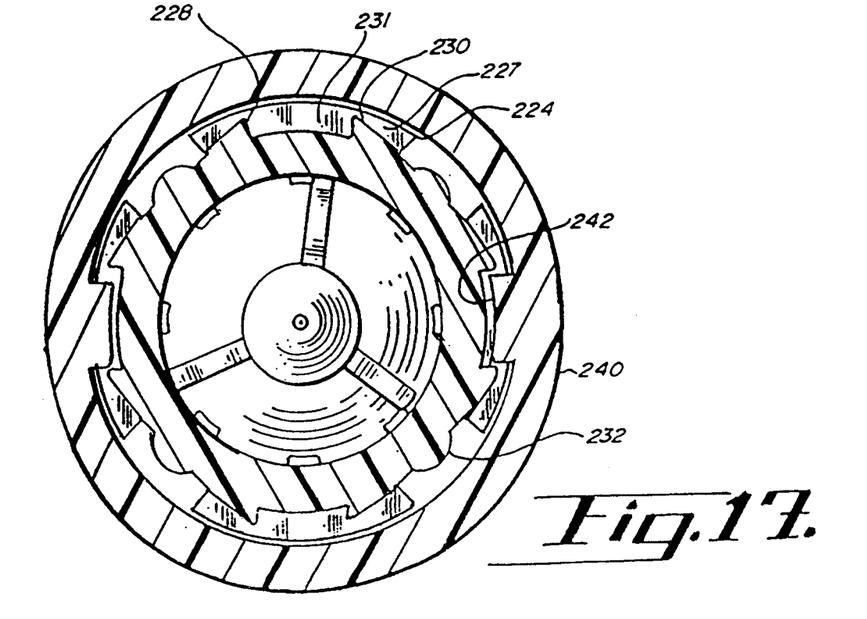
FIG. 17 is a cross-sectional view taken generally along lines 16—16 of FIG. 12 showing the collar and needle shield of the present embodiment with the needle shield in the locked and extended position.

Next, when the needle shield 240 is in the retracted position, the syringe may be used in a conventional manner to draw and inject a medication into the patient. Alternately, the needle shield 240 may be moved from the retracted position to the releasable extended position to safely transport the medication containing syringe to the patient, as described above. Once the needle shield 240 is in the retracted position and the injection has been completed, the needle shield 240 may be moved to the extended position so that the keys 242 slide in the keyways 225 and over the spherical detents 232 between the adjacent protrusions 224 on the collar 222 and so that the longitudinal detents 250 slide over the protrusions 224 as described above. To lock the needle shield 240 in the extended position, the user may rotate the needle shield 240 in either direction about the syringe barrel 210 to cause the proximal ends 248 of the keys 242 to move over the adjacent wall members 228 or 230 until the proximal ends 248 of the keys 242 fall into the locking slots 231 formed between the wall members 228 and 230 (FIG. 17). When the keys 242 are positioned in the locking slots 231, the proximal end 248 of each key 242 abuts against the squared-off stop surface 227 of one of the triangular protrusions 224 on the collar 222 and against the perpendicular wall surface of the wall members 228 and 230 so that the needle shield 240 cannot be rotated or returned to its retracted position without the application of excessive force. Finally, the user may return the needle sheath 264 to the distal end of the needle shield 240 as described above to allow for the safe disposal of the entire assembly.

What is claimed is:

1. A needle shielding device for use with a barrel, wherein a needle is attached to the forward end of the barrel, the improvement comprising:
   a separate shield retaining means mounted on said barrel and including at least one locking slot on its outer surface,
   an elongated needle shield having distal and proximal ends wherein said shield is movable over said barrel and retaining means between a retracted position in which the needle is exposed and an extended position in which said shield protects said needle, said shield including at least one elongated key on its interior surface, said key adapted to slide in a path outside said locking slot and being rotatable into said locking slot when said shield is in its extended position; and
   an elongate needle protecting needle sheath having an open proximal end and a closed distal end wherein said need sheath is removably mounted on said distal end of said shield and said shield is movable between said retracted and extended positions with said needle sheath mounted thereon.

2. The needle shielding device according to claim 1 wherein said locking slot comprises a pair of opposed walls at least one of which includes a ramp-shaped surface over which said key can ride when said needle shield is rotated, and a protrusion positioned proximally of said locking slot for preventing said shield from being movable to the retracted position after said key has been rotated into said locking slot.

3. The needle shielding device according to claim 2 wherein each of said opposed walls includes a ramp-shaped surface so that said key on said needle shield may be rotated in either direction into one of said locking slots.

4. The needle shielding device according to claim 1 wherein said shield includes an inwardly extending detent on its interior surface and said shield retaining means includes a surface adapted to abut against said detent to releasably retain said sleeve in the retracted position.

5. The needle shielding device according to claim 1 wherein said shield retaining means includes at least one detent extending from its outer surface adapted to abut against said key when said shield is in the extended position.

6. The needle shielding device according to claim 1 wherein said proximal end of said shield includes an inwardly extending rim adapted to abut against said proximal end of said shield retaining means to limit the forward movement of said shield.

7. The needle shielding device according to claim 6 further including a means for preventing rotation of said shield when said shield is in the retracted position.

8. The needle shielding device according to claim 3 wherein said means for preventing rotation comprises radially extending projections on the exterior surface of said shield retaining means.

9. The needle shielding device according to claim 7 wherein said means for preventing rotation of said needle shield also prevents said rotation of said needle shield as said needle shield is moved between the retracted and extended positions.

10. The needle shielding device according to claim 1 wherein said shield retaining means is separate from said barrel and wherein there is provided an interlocking means on said shield retaining means and barrel for preventing rotation of said shield retaining means about said barrel.

11. The needle shielding device according to claim 1 wherein said needle shield includes a radially extending finger flange on the exterior surface thereof.

12. A medical device comprising:
    a syringe including an elongate barrel having distal and proximal ends, a plunger slidable within said barrel, and a needle having a distal needle point thereon wherein said needle is attached to said distal end of said barrel,
    a collar operatively associated with said distal end of said barrel and including a plurality of locking slots on the outer surface of said collar, each of said locking slots being formed by a pair of opposed walls on said collar,
    an elongated needle shield movable over said barrel and said collar between a retracted position wherein said needle point is exposed and an extended position wherein said needle point is protected, said shield including a plurality of elongated keys on its interior surface, each of said keys being adapted to slide in a keyway displaced circumferentially from said locking slots on said collar and wherein at least one of said keys being rotatable into one of said locking slots when said shield is in its extended position, and
    a needle sheath having a closed distal end and an open proximal end wherein said open proximal end is mounted on said needle shield to protect said needle point when said shield is in the retracted position and wherein said shield and needle sheath are movable between said retracted and extended positions with said needle sheath protecting said needle when said shield is in said retracted position.

13. The combination according to claim 12 wherein each of said opposed walls includes a ramp-shaped surface so that said keys can be rotated in either direction into said locking slots.

14. The combination according to claim 12 wherein a retaining means is located on said collar and said shield for releasably retaining said shield in said retracted position.

15. The combination according to claim 12 wherein said collar includes at least one detent on its outer surface adapted to abut against one of said keys when said shield is in said extended position.

16. The combination according to claim 12 wherein said shield includes end walls at its distal and proximal ends to prevent the movement of said shield beyond said retracted and extended positions.

17. The combination according to claim 12 wherein said shield includes a radially outwardly extending finger flange thereon to facilitate the operative movement of said shield between said retracted and extended positions.

18. The combination according to claim 12 wherein said collar further includes a plurality of protrusion extending radially outwardly therefrom and wherein said protrusions are spaced apart to form keypads therebetween to enable said keys to slide therethrough.

19. A medical device comprising:

a syringe having distal and proximal ends and including a tubular barrel section, a plunger slidable within said barrel section, and a needle having a distal needle point thereon wherein said needle is attached to said distal end of said syringe, a collar having distal and proximal ends operatively associated with said distal end of said syringe, said distal end of said collar including a plurality of locking slots thereon and a plurality of protrusions along said collar wherein said protrusions are spaced apart on said collar to form a plurality of keyways therebetween, an elongated needle shield having distal and proximal ends movable over said barrel section and said collar between a retracted position in which said needle point is exposed and an extended position wherein said needle point is protected, said shield including a plurality of elongated keys on its interior surface, said keys being adapted to slide in said keyways formed between said protrusions on said collar wherein each of said keys are rotatable into one of said locking slots when said shield is in said extended position, and a needle sheath having an open proximal end and a closed distal end wherein said open proximal end is removably mounted to said distal end of said shield and said shield is movable between said retracted and extended positions with said needle sheath mounted thereon.

20. The combination according to claim 19 wherein said collar and said shield include means thereon for releasably retaining said shield in said retracted position.

21. In combination, a syringe having distal and proximal ends including a barrel section therebetween, and a needle having a distal needle point wherein said needle is attached to the distal end of said syringe, collar means operatively associated with said syringe, an elongated needle shield having distal and proximal ends movable over said barrel section and said collar between a retracted position wherein said needle point is exposed and an extended position wherein said needle point is protected, means for orienting said shield in slidable alignment along said collar means wherein rotation of said shield about said barrel section is prevented as said shield is moved between said retracted and extended positions, locking means on one of said collar means or said shield to lock said shield in said extended position when said shield is in said extended position and rotated about said barrel section, and a needle sheath having an open proximal end and a closed distal end wherein said open proximal end is mountable on said distal end of said shield and said shield is movable between said retracted and extended positions with said sheath mounted thereon.

22. A method of using a safety syringe including an elongate barrel having distal and proximal ends with a needle mounted on the distal end thereof and an elongate and tubular needle shield having distal and proximal ends slidably mounted about said barrel and including a needle sheath mounted on the distal end of the needle shield, the method including the steps of:

sliding the needle shield and needle sheath from a retracted position wherein the needle extends distally beyond the needle shield and the needle sheath protects the needle to an extended position wherein the needle shield protects the needle, removing a needle sheath from the distal end of the needle shield, filling the syringe with a desired medication, and moving the needle shield proximally along the barrel to an extended position wherein the needle shield protects the needle of the syringe.

23. The method of claim 22 further including the step of removing the needle sheath from the distal end of the needle shield when the needle shield is in a releasable and extended position and moving the needle shield to a retracted position wherein the needle is exposed to enable the user to fill the syringe and inject the medication into the patient.

24. The method of claim 23 further including the steps of:

moving the needle shield to the extended needle protecting position after injecting the medication into the patient, rotating the needle shield about the barrel to move the needle shield to a locked and extended position, and placing the needle sheath on the distal end of the needle shield while the needle shield is in the locked and extended position.

25. A method of using a safety syringe having an elongate barrel member including distal and proximal ends with a needle mounted on the distal end thereof and an elongate needle shield having distal and proximal ends slidably mounted about said barrel member and including a needle sheath mounted thereon, the method including the steps of:

sliding the needle shield and needle sheath from an initial retracted position wherein the needle extends distally beyond the distal end of the needle shield and is protected by the needle sheath to an extended position wherein the needle is protected by the needle shield, removing a needle protecting needle sheath from the distal end of the needle shield, filling the safety syringe with a desired medication, injecting the patient with the desired medication, sliding the needle shield along the barrel to an extended position wherein the needle is protected by the needle shield, and rotating the needle shield about the barrel to place the needle shield in a locked and extended position.

* * * * *

UNITED STATES PATENT AND TRADEMARK OFFICE
CERTIFICATE OF CORRECTION

PATENT NO. : 5,147,326
DATED : September 15, 1992
INVENTOR(S) : Talonn et al

It is certified that error appears in the above-identified patent and that said Letters Patent is hereby corrected as shown below:

On the title page, Item [63] Ser.No. 212,524, should be changed to Ser, No. 212,528.

Signed and Sealed this

Fifth Day of October, 1993

Attest:

BRUCE LEHMAN

Attesting Officer     Commissioner of Patents and Trademarks